United States Patent [19]

Suyama

[11] Patent Number: 5,728,080

[45] Date of Patent: Mar. 17, 1998

[54] DEGASSING DEVICE FOR AN ARTIFICIAL ANAL BAG

[75] Inventor: Masuhiro Suyama, Nagano, Japan

[73] Assignee: Suyamasaburoshoten Co., Ltd., Nagano, Japan

[21] Appl. No.: 571,930

[22] PCT Filed: Jun. 28, 1994

[86] PCT No.: PCT/JP94/01038

§ 371 Date: Jun. 17, 1996

§ 102(e) Date: Jun. 17, 1996

[87] PCT Pub. No.: WO95/01142

PCT Pub. Date: Jan. 12, 1995

[30] Foreign Application Priority Data

Jun. 30, 1993 [JP] Japan ........................... 5-188761
Mar. 8, 1994 [JP] Japan ........................... 6-064641

[51] Int. Cl.$^6$ ........................................ A61F 5/44
[52] U.S. Cl. .............................................. 604/333
[58] Field of Search ........................ 604/323–327, 604/332, 333, 277

[56] References Cited

U.S. PATENT DOCUMENTS

| | | | |
|---|---|---|---|
| 2,476,375 | 7/1949 | Kent | 604/353 |
| 4,636,313 | 1/1987 | Vaillancourt | 604/323 |
| 5,470,325 | 11/1995 | Fundock | 604/332 |

FOREIGN PATENT DOCUMENTS 1363644  8/1974  United Kingdom ................. 604/333

Primary Examiner—Robert A. Clarke
Attorney, Agent, or Firm—Jones, Tullar & Cooper, P.C.

[57] ABSTRACT

The present invention relates to a degassing device for an artificial anal bag which is capable of storing the gas generated in the intestines, and of discharging the gas from the bag at a selected place where degassing causes no nuisance to others.

It comprises an elongated tube having a filter loaded therein, an opening-and-closing plug attached to its head end and a diverging joint formed at its tail end. The diverging joint can be attached to the circumference of a joint opening, which is made in the upper part of the bag.

When the bag is inflated with the gas and excreta from the intestines, the patient can go to the men's room or somewhere for discharging the gas from the bag. Then, the excreta and liquid content are prevented from passing through the filter, only permitting the gas to flow therethrough. Thus, degassing can be put under the perfect control by the patient, so that there is no fear of permitting leakage of gas to cause nuisance to others or imprignation of his underwear with unpleasing odor before the patient is aware.

3 Claims, 5 Drawing Sheets

A-A

DEGASSING DEVICE FOR AN ARTIFICIAL ANAL BAG

This application claims the benefit of international application PCT/JP94/01,038 which international application was filed 28, Jun. 1994.

BACKGROUND OF THE INVENTION

1. Field of the Invention

The present invention relates to an artificial anal bag for containing the solid and liquid waste matter passed from the artificial anus, and more particularly to an improvement in or relating to a degassing device for permitting the discharging of gas of unpleasant odor from the bag.

2. Description of the Prior Art

There are two different types of artificial anal bags for containing the solid and liquid waste matter excreted from the artificial anus, that is, the direct application type of bag to be attached directly to a patient's body, and a two-piece type bag comprising an annular-ridged piece to be attached to the circumference of the artificial anus and a bag having a counter annular recess to permit the fitting-in of the annular-ridged piece.

As for the two-piece type of bag the bag is freely rotatable by its annular recess about the the annular ridge of the artificial anus, and therefore, the bag is permitted to take any position appropriate for the patient's posture no matter in what way they may hold their body while lying in bed or standing or walking.

Also, there are two different types of bags, that is, a closed bag (see FIG. 8) and a bottomless bag (see FIG. 9). Closed bags are disposable. In contrast, bottomless bags can be repeatedly washed and used, and are called "U-type bag".

The bags 20 shown in FIGS. 8 and 9 is made of sheet material which is not pervious to liquid and gas, and it has an opening 21 made on its rear side. The artificial anus, which is called "Stoma" (not shown), is exposed from the cut in the abdominal region of the patient to be connected to the circumference of the opening 21 of the bag 1. Before use a separable or peeling-off piece of paper is applied to the two-sided adhesive tape 22, which is applied to the opening 21 of the bag 20.

A piece of sponge 23 is made of a soft fiber material, which is capable of absorbing liquid, and permitting gas to pass therethrough. The sponge 23 is impregnated with activated charcoal. The bag 20 has small ventilating holes 24 made in a small circular area at one corner of the bag 20, in FIG. 8, or in a rectangular area at the top, center of the bag 20, as seen in FIG. 9. The sponge 23 is applied to the inside of the bag 20 by an adhesive agent so as to cover the ventilating holes 24.

As for the bottomless bag 20 of FIG. 9 it is used with its open bottom bent and pinched with a clip 30. When the bag 20 is filled with solid and liquid waste matter excreted from the artificial anus, it is removed from the patient, and then the clip 30 is removed for discharging the content. The bag 20 is washed and dried for reuse.

Before attaching such a bag 20 to a patient, the skin around the artificial anus is cleaned, and then, the separable piece of paper is peeled off from the circumference of the opening 21 of the bag 20. The bag 20 is applied to the patient with the aid of the two-sided adhesive tape 22. Thus, the bag 20 is connected to the artificial anus via its opening 21.

As the artificial anus has no means of controlling the discharging of excreta, the patient excretes without being aware of excretion, thus allowing excreta to be accumulated in the bag 20. Likewise, gas generated in the intestines is released into the bag 20 via the artificial anus to be accumulated therein. Usually the bag 20 is filled with such gas in two hours.

As the gas is accumulated in the bag 20, the inner pressure of the bag 20 increases until it leaks from the bag 20 through the ventilating holes 24. Japanese Patent Application, Publication Nos. 61-22580 and 4-60659, and Japanese Utility Model Application, Publication Nos. 60-34258 and 57-128819 proposed artificial anal bags which are designed to permit leakage of the gas without accompanying excreta while the patient is sleeping in bed, and are designed to remove the unpleasant odor from the leaking gas.

Leakage of the gas from such bags, however, cannot be controlled by patients. The odor can be removed from the leaking gas by activated charcoal in the sponge 23. As a matter of fact, however, such activated charcoal is likely to lose the effect of removing unpleasant odor from the gas in a few hours, thus permitting leakage of the gas from the ventilating holes 24 without removing the unpleasant odor.

The gas passes between the underwear and the patient's body, rising up to his neck. Even if the patient goes to the men's room for degassing immediately after being aware of leakage of the gas from the bag, his underwear has been already impregnated with the unpleasant odor.

Complete odor removal requires a relatively large amount of activated charcoal, and accordingly the bag size must be increased. Apparently this causes inconvenience for patient's mobility, making such bags less practical in use.

When such an odor-removing agent is changed, the bag must be removed from the patient, and washed, and then, the old sponge must be removed and changed for a new one. This is tedious work.

Still disadvantageously, accumulation of gas in the bag raises its inner pressure so that the discharging of excreta into the bag may be increasingly difficult, and therefore, the patient must be careful all the time lest the bag should be filled with gas.

When activated charcoal gets wet, it will lose the effect of removing odor from gas, thus allowing leakage of gas without completely removing the odor from the leaking gas.

The conventional bags have no means to control release of gas from the bag.

SUMMARY OF THE INVENTION

In view of the above one object of the present invention is to provide a bag equipped with means to permit the patient to control release of the gas from the bag, thus permitting the patient to release the gas from the bag at a selected place where degassing causes no nuisance to others.

A degassing device according to the present invention is constructed as follows:

A degassing tube has a filter loaded therein, and it has an opening-and-closing plug attached to its head end and a diverging joint attached to its tail end. The bag has a joint opening made on its upper part, and the degassing tube is connected to the bag by attaching the diverging joint of the tube to the circumference of the joint opening of the bag.

First, a joint opening is made by scissoring a selected part of the bag, and the diverging joint of the degassing tube is connected to the circumference of the joint opening thus made in the bag.

When the bag is used, gas and excreta from the bowels flow into the bag, thereby expanding the bag. If the patient feels that the bag is expanding, he goes to a certain place such as a men's room, where he turns the opening-and-closing plug to release the gas from the bag.

The patient had better go to the men's room every two or three hours for degassing even if the bag is not filled with gas. Even if the bag is not so inflated, the patient can release the gas easily by giving a gentle push to the bag. After degassing the patient closes the plug, and he puts the bag in place.

BRIEF DESCRIPTION OF THE DRAWINGS

Other objects and advantages of the present invention may be understood from the following description of a preferred embodiment which is shown in the accompanying drawings.

DETAILED DESCRIPTION OF PREFERRED EMBODIMENTS

Figure 1:
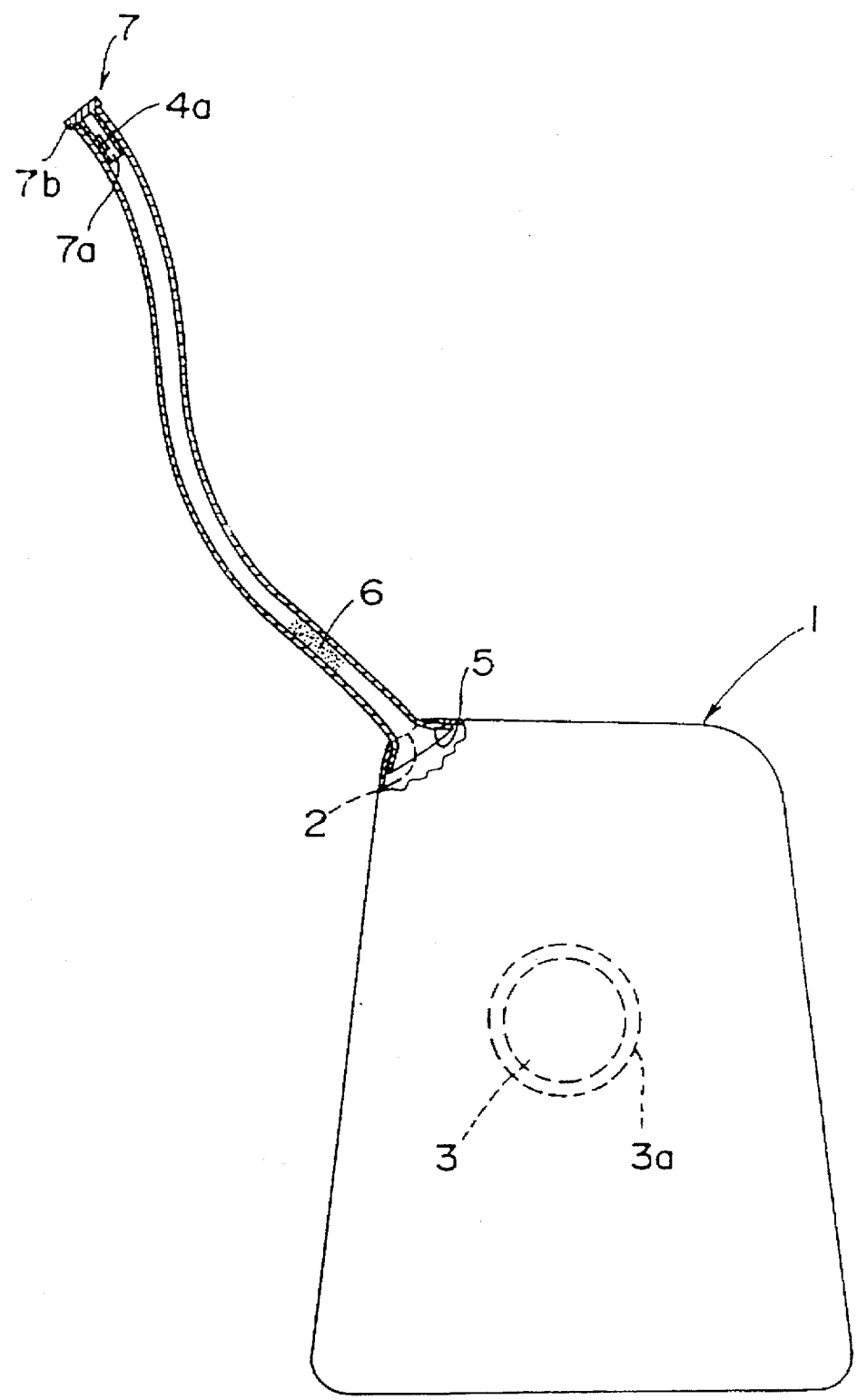
FIG. 1 shows an artificial anal bag, partly in section according to the present invention.
Figure 2:
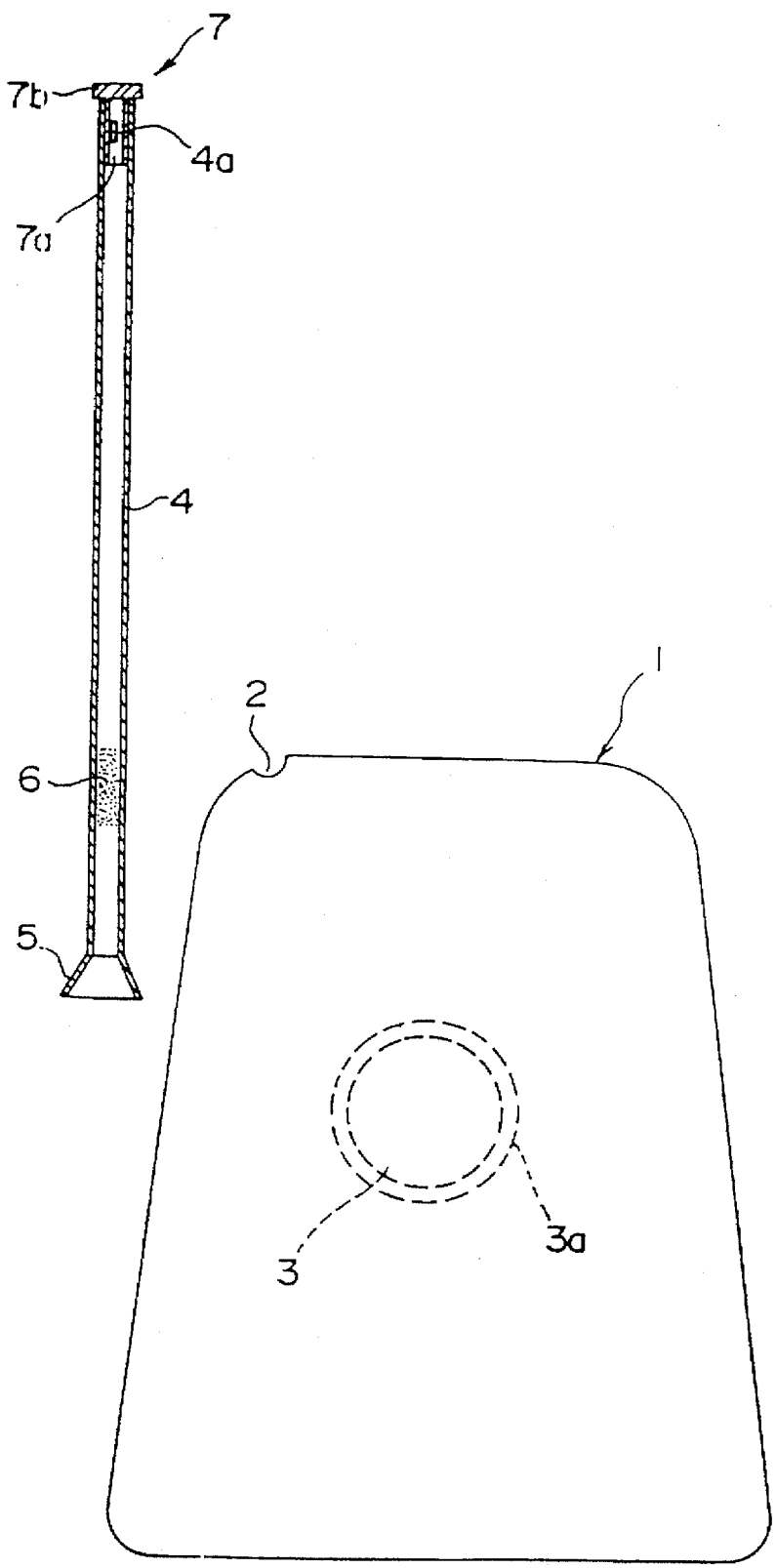
FIG. 2 shows the artificial anal bag of FIG. 1 in disassembling condition, partly in section.
Figure 3:
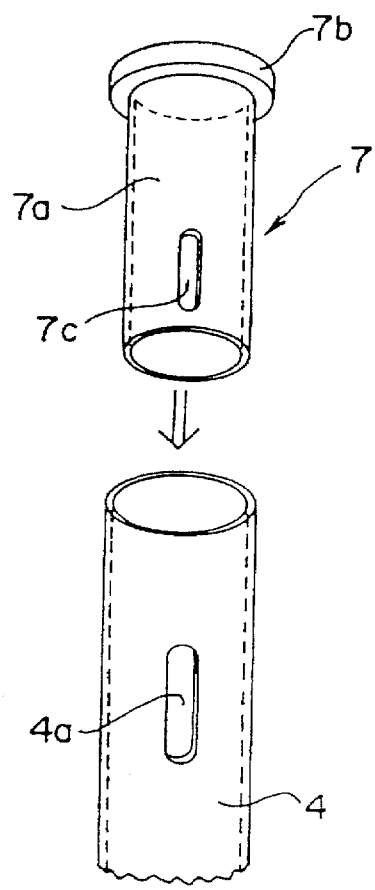
FIG. 3 is a perspective enlarged view of an opening-and-closing plug.

FIGS. 1 and 2 show a bag for an artificial anus in assembled and disassembled conditions respectively.

An artificial anal bag 1 has a tube-joint opening 2 at its upper portion, and a center, circular opening 3 on its rear side. The circular opening 3 has a soft, both-sided adhesive tape 3a attached on its circumference, and the adhesive tape 3a has a separable piece of paper to be peeled off upon application the bag 1 to the artificial anus. The tube-joint opening 2 is made apart from the center opening 3, preferably at the upper, left corner of the bag 1. A degassing tube 4 is a soft, flexible tube, and is 10 to 80 centimeters long. It has a diverging joint end 5. The joint opening 2 is of the same size as the degassing tube 4.

The degassing tube 4 has a filter 6 loaded therein, and the filter 6 is of a sponge material which is impervious to liquid, but pervious to gas. All parts described above are preferably soft enough to give a pleasing touch to the patient.

Figure 4:
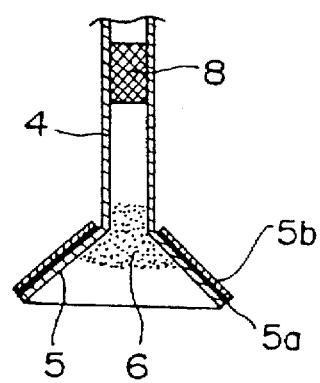
FIG. 4 is an enlarged section of the tube-to-bag joint in FIG. 1.

A relatively small amount of filter material can be pushed in the degassing tube (see FIG. 2) whereas a relatively large amount of filter material can be put on the inlet of the diverging joint 5 of the degassing tube (see FIG. 4).

A plastic opening-and-closing plug 7 is attached to the head end of the degassing tube, and it comprises a cylindrical body 7a and an enlarged head cap 7b. The cylindrical body 7a has an elongated opening 7c for degassing use. Also, a similar elongated opening 4a is made in the vicinity of the tube end at such a position that the plug 7 can be pushed into the tube end with their elongated openings 7a and 4a registered with each other. Thus, the opening-and-closing plug 7 can be rotated to an opening or closing position with respect to the elongated opening 7 of the degassing tube 4.

Figure 5:
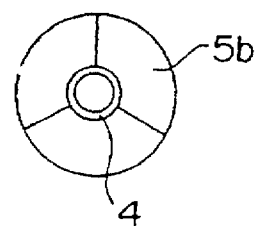
FIG. 5 is a bottom view of the tube-to-bag joint.

FIG. 4 shows details of the tube-to-bag joint 5 to an enlarged scale, and FIG. 5 is a bottom view of the diverging joint end. It has a two-sided adhesive tape 5a on its circumference, and an annular separable piece of paper 5b is put on the tape 5a to cover the same.

The degassing tube 4 having no plug 7 attached thereto is put in the bag 1 from the center opening 3, and the tube 4 is pulled out of the joint opening 2 of the bag 1 until the diverging joint 5 comes close to the joint opening 2 of the bag 1. The separable piece of paper 5b is removed from the circumference of the diverging joint 5 to be applied to the circumference of the joint opening 2, thereby sealing the circumference of the joint opening 2 inside of the bag 1. Thus, the degassing tube 4 is connected to the bag 1 in a liquid-and-air tight way.

The diverging joint 5 is attached to the inside of the bag 1, and there is no fear of the tube being removed from the bag even if a pull is applied to the tube.

An odor removing agent 8 is loaded in the degassing tube 4. Usually activated charcoal is used as an odor removing agent 8. The odor removing agent 8 is preferably positioned apart from the filter 6 lest it should be wet with excreta in the bag 1.

Finally the opening-and-closing plug 7 is attached to the head end of the degassing tube 4.

In use the separable piece of paper 3a is removed from the circumference of the center opening 3, and the bag 1 is applied to the artificial anus. The bag 1 is fixed to the patient's body by expandable bands or underwears, thereby preventing undesired displacing of the bag. The head length of the degassing tube 4 may be pulled out and held under the cord or band around the patient's waist. If the degassing tube 4 is relatively long, it may be pulled out of the collar of the underwear, and the head length of the degassing tube 4 may be held under the cord or band around the patient's waist.

When the bag 1 is inflated with gas, the gas is allowed to flow in the degassing tube 4 via the filter 6, but excreta is prevented from flowing in the degassing tube 4 by the filter 6.

Then, the patient feels the bag 1 inflating, and he goes to the men's room or somewhere to take the head end of the degassing tube 4 out of his underwear. The gas is released by turning the opening-and-closing plug 7 to the opening position, and finally the gas is forced to flow out by giving a gentle push to the bag 1. Then, there is no fear of allowing excreta to flow out because of the existence of the traversing filter 6.

It should be noted that the opening-and-closing plug 4 is not limited to this particular structure, and that any means appropriate for switching the discharging of the gas to the blocking of gas flow or vice versa may be used.

Figure 6:
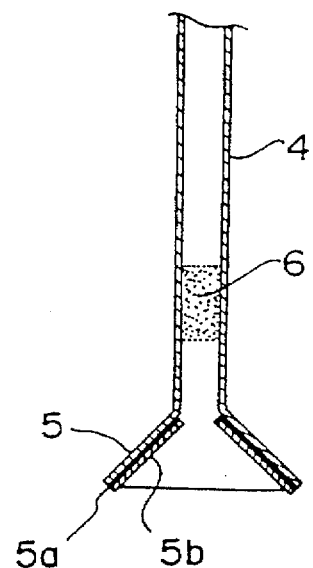
FIG. 6 is an enlarged section of another tube-to-bag joint.

FIG. 6 shows another example of the tube-to-bag joint 5 to an enlarged scale. The diverging joint 5 has a two-sided tape 5a on its inner circumference. The separable piece of paper 5b is peeled off, and the diverging joint 5 is applied to the outer circumference of the joint opening 2 of the bag 1. This type of diverging joint 5 is appropriate for use in a relatively small bag, and it can be attached to the bag with ease.

Figure 7:
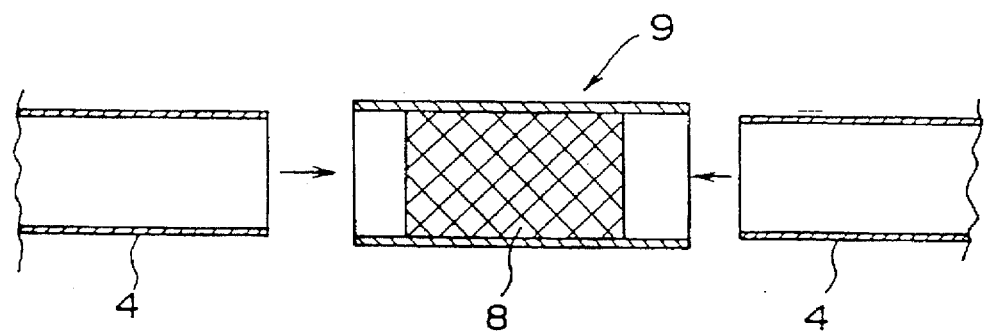
FIG. 7 is an enlarged section of a selected part of another degassing tube.
Figure 8:
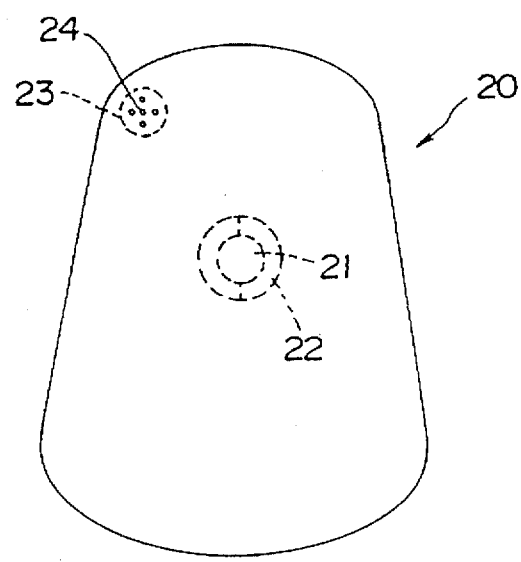
FIG. 8 is a plane view of a conventional artificial anal bag.
Figure 9:
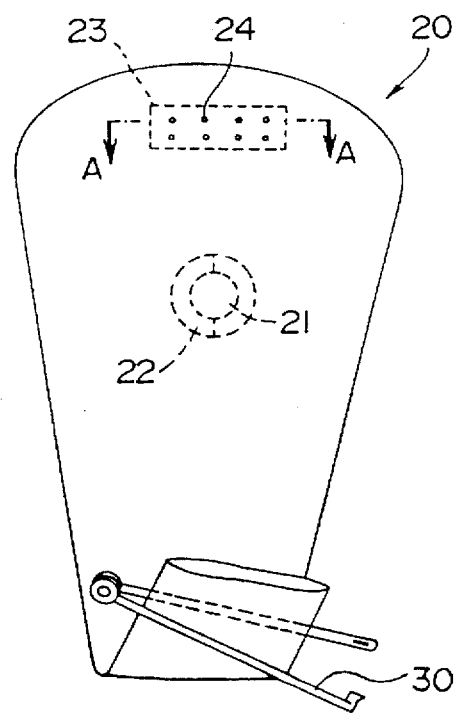
FIG. 9 is a plane view of another conventional artificial anal bag.
Figure 10:
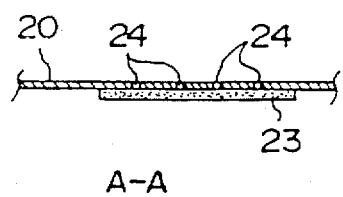
FIG. 10 is an enlarged section of the artificial anal bag taken along the line A—A in FIG. 9.

FIG. 7 shows another example of a degassing tube to an enlarged scale. This degassing tube is designed so as to facilitate the changing of the odor removing agent. Specifically it comprises two separate parts connected by an intermediate tube 9, which is loaded with the odor removing agent 8. The intermediate tube 9 may be a cylindrical container having perforated covers at its opposite ends for ventilation, and particles of odor removing agent 8 may be contained therein. Alternatively odor removing agent 8 may be formed to be a encapsulated solid.

The patient may have new intermediate tubes or odor removing capsules with him, so that odor removers may be ready to be changed when old ones lose their capabilities of removing odor.

As may be understood from the above, the excreta and gas generated in the intestines are stored in the artificial anal bag before the patient is aware, but when he feels the bag inflating or judging from the length of time passed after the last degassing, he goes to the men's room or somewhere for degassing. Even if no odor removing agent is used, there is no fear of causing a nuisance to others, and of causing his underwear to be impregnated with an unpleasant odor.

No excreta or liquid content is allowed to pass through the filter, and only gas is allowed to pass through the filter, finally being allowed to flow out by opening the plug. Thus, degassing can be placed under perfect control by the patient, thereby removing his anxiety.

Artificial anal bags equipped with degassing means according to the present invention are simple in structure, and advantageous to mass production. Also advantageously, the joint opening can be made by scissoring a selected upper part of the bag to fit the size of the tube to be attached, and therefore, any kind of artificial anus bag can be used simply by making a joint opening in the bag.

What is claimed is:

1. An artificial anal bag and degassing device, comprising: a bag having an upper part and a joint opening at its upper part; an elongated tube having a head end and a tail end and a filter loaded therein; and an opening-and-closing plug attached to said head end, said elongated tube having a diverging joint formed at said tail end, said diverging joint being adapted to be attached to the circumference of said joint opening inside of said bag.

2. The artificial anal bag and degassing joint as defined in claim 1, further comprising: two-sided adhesive tape included as part of the outer circumference of said diverging joint, said two-sided adhesive tape having a separable piece of paper covering one adhesive surface.

3. The artificial anal bag and degassing joint as defined in claim 1, further comprising: two-sided adhesive tape included as part of the inner circumference of said diverging joint, said two-sided adhesive tape having a separable piece of paper covering one adhesive surface.

* * * * *